United States Patent [19]

Drake

[11] Patent Number: 4,490,567

[45] Date of Patent: Dec. 25, 1984

[54] CATALYST AND PROCESS FOR DEHYDRATING 2-ALCOHOLS

[75] Inventor: Charles A. Drake, Bartlesville, Okla.

[73] Assignee: Phillips Petroleum Company, Bartlesville, Okla.

[21] Appl. No.: 366,513

[22] Filed: Apr. 8, 1982

[51] Int. Cl.$^3$ .............................................. C07C 1/00
[52] U.S. Cl. .................................... 585/324; 585/640
[58] Field of Search ............................... 585/640, 324

[56] References Cited

U.S. PATENT DOCUMENTS

| | | | |
|---|---|---|---|
| 1,895,529 | 1/1933 | Taylor et al. | 585/640 |
| 1,914,722 | 6/1933 | Jaeger | 585/640 |
| 2,377,026 | 5/1945 | Miller | 585/640 |
| 2,963,524 | 12/1960 | Shakelford et al. | 585/640 |
| 3,283,027 | 12/1962 | Lundeen et al. | 585/640 |
| 3,294,588 | 2/1974 | Stiles . | |
| 3,457,320 | 7/1969 | Stapp et al. | 585/329 |
| 3,529,033 | 9/1970 | Frilette et al. | 585/640 |
| 3,600,455 | 8/1971 | Dean | 585/640 |
| 3,658,392 | 4/1972 | Arganbright et al. | 305/24 |
| 3,849,512 | 11/1974 | Bowman | 585/611 |
| 3,947,347 | 3/1976 | Mitchell | 208/251 H |
| 4,008,254 | 2/1977 | Gross et al. | 549/460 |
| 4,013,694 | 3/1977 | Fishel | 549/460 |
| 4,061,594 | 12/1977 | Michel . | |
| 4,234,752 | 11/1980 | Wu et al. | 585/640 |

FOREIGN PATENT DOCUMENTS

| | | | |
|---|---|---|---|
| 1278981 | 6/1972 | France . | |
| 917047 | 1/1963 | United Kingdom | 585/640 |
| 1233020 | 5/1981 | United Kingdom | 585/640 |

*Primary Examiner*—Delbert E. Gantz
*Assistant Examiner*—Cynthia A. Prezlock
*Attorney, Agent, or Firm*—Edward L. Bowman

[57] ABSTRACT

Novel catalysts are disclosed for the selective dehydration of 2-alcohols to α-olefins. In one case, the catalyst comprises at least one catalytic metal oxide on a low surface area aluminum oxide-containing support. In another case, the catalyst comprises a mixture of thorium oxide and cerium oxide on a base treated aluminum oxide containing support. There is also disclosed a novel process for obtaining high purity 4-methyl-1-pentene involving the dehydration of 4-methyl-2-pentanol followed by disproportionation with ethylene.

35 Claims, No Drawings

CATALYST AND PROCESS FOR DEHYDRATING 2-ALCOHOLS

BACKGROUND OF THE INVENTION

This invention relates to the production of α-olefins by the catalytic dehydration of 2-alcohols.

It is well known that alcohols may be dehydrated to produce monoolefinic materials by passing the alcohols over the heated oxides of certain metals, such as aluminum oxide, thorium oxide, silicon dioxide, titanium oxide, magnesium oxide, tungsten oxide, chromium oxide, and zirconium oxide or mixtures thereof. The prior technical literature on the subject of this type of catalytic dehydration indicates that alumina, thoria and several of the other metal oxides and equivalents in their dehydrating effect and usually may be used interchangeably. Pines and Haag have reported in a paper published at page 2847 of volume 83 of the Journal of the American Chemical Society (1961) that α-olefins (terminally unsaturated olefins) may be obtained by dehydrating primary alcohols over an alumina catalyst. These workers further state that when 2-alcohols are dehydrated over the alumina catalyst, a mixture of internal olefin and α-olefin results, with the more stable internal olefin predominating over the α-olefin. Obtaining a dehydration product in which the α-olefin predominates significantly is a challenge since the internal olefin product is the thermodynamically favored product.

U.S. Pat. No. 3,283,027 discloses that thorium oxide and a number of other metal oxides including cerium oxide and other oxides of the rare earths possess the capability of catalyzing the selective dehydration of 2-alcohols to α-olefins.

Such catalysts have been found to have several disadvantages. For example, thorium oxide is a very insoluble material which makes it a difficult material to apply to a support. Further, when thorium oxide was applied to glass bead support as shown in Example 4 of that patent, it was noted that the catalyst was quite fragile and that thoria fell off the glass beads and caused reactor plugging. When the thorium oxideglass bead catalyst was employed as a catalyst in the dehydration of 4-methyl-2-pentanol, it was noted that at atmospheric pressure the conversion was quite low even at high reaction temperature. In order to actually be commercially attractive, the dehydration catalyst should be durable and should give good conversion and selectivity at atmospheric pressure.

An object of the present invention is to provide a dehydration catalyst that is durable and that is capable of giving good conversion and selectivity to α-olefin even at atmospheric pressure.

Another object is to provide a method for the production of 4-methyl-1-pentene and 3-methyl-1-butene in various ratios from 4-methyl-2-pentanol and ethylene.

SUMMARY OF THE INVENTION

In accordance with the present invention, there is provided a catalyst for the selective dehydration of 2-alcohols to α-olefins comprising a catalytically effective amount of at least one metal oxide wherein the metal is selected from the group consisting of metals having atomic numbers of 21, 39, 58-71, or 90 supported on a support comprising an oxide of alumina and further being characterized by having a surface area no greater than 20 m²/gm as determined by the BET nitrogen adsorption technique.

In accordance with yet another embodiment of the present invention, there is provided a catalyst for the selective dehydration of 2-alcohols to 60-olefins comprising a catalytically effective amount of a mixture of thorium oxide and cerium oxide supported on a support comprising a base treated oxide of alumina.

In accordance with yet another embodiment of the present invention, there is provided a method for the production of 4-methyl-1-pentene and 3-methyl-1-butene by the dehydration of 4-methyl-2-pentanol over a dehydration catalyst and then contacting the resulting mixture of 4-methyl-1-pentene and 4-methyl-2-pentene with ethylene in the presence of a disproportionation catalyst under conditions sufficient to promote conversion of 4-methyl-2-pentene to a mixture of 3-methyl-1-butene and propylene, wherein said dehydration catalyst is selective to 4-methyl-1-pentene production when large yields of 4-methyl-1-pentene are desired or to 4-methyl-2-pentene when large yields of 3-methyl-1-butene are desired.

DETAILED DESCRIPTION

The support used in the preferred embodiment of the present invention can be any suitable support containing an oxide of alumina which has a surface area no greater than about 20 m²/gm, preferably no greater than 5 m²/gm. Included within the scope of the invention are thus the low surface area aluminas and combinations of aluminium oxide and silicon oxide having low surface area. The preferred supports are those comprising α-alumina, especially those having a surface area of no greater than 1 m²/gm. In a particularly preferred embodiment, the support is treated with a basic compound of a metal of Groups I and II of the Periodic Table.

The catalytically active metal oxides that are deposited on the defined support are selected from the group consisting of thorium oxide, scandium oxide, yttrium oxide, and the oxides of the rare earth metals, cerium, praseodymium, neodymium, prometheum, samarium, europium, gadolinium, terbium, dysprosium, holmium, erbium, thulium, ytterbium, and lutecium. Typical examples include $Ce_2O_3$, $CeO_2$, $Dy_2O_3$, $Er_2O_3$, $Eu_2O_3$, $EuO$, $Gd_2O_3$, $Ho_2O$, $Lu_2O_3$, $Nd_2O_3$, $Pr_2O_3$, $PrO_2$, $Pr_6O_{11}$, $Sm_2O_3$, $SmO$, $Tb_2O_3$, $TbO_2$, $Tb_4O$, $Tm_2O_3$, $Yb_2O_3$, $YbO$, $Se_2O_3$, $Y_2O_3$, and $ThO_2$.

The catalyst is considered to be effective for the dehydration of any 2-alcohol that is capable of being dehydrated to an alpha olefin. Examples of such 2-alcohols are those of the formula

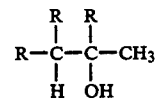

wherein at least one R is hydrocarbon in nature and wherein each R is individually selected from the group consisting of hydrogen, hydrocarbon radicals, and substituted hydrocarbon radicals wherein the substituents are selected from the keto, hydroxyl, alkoxy, and ester groups. Typically in order for 2-alcohols to be capable of being dehydrated to alpha olefins, aryl groups should be attached only at the number 4 position or a higher position, keto groups should be attached only at the number 5 position or a higher position, carbon-carbon olefinic or acetylenic unsaturation, hydroxyl groups, and ester groups should be attached only at the number 6 or higher position and preferably the number 7 or higher position. Obviously, the R on the 2 position carbon must be either H or a methyl group in order for the alcohol to be a 2-alcohol.

Typically, the hydrocarbyl radicals and the substituted hydrocarbyl radicals in the above formula would contain 1 to 17 carbon atoms. Generally, the preferred 2-alcohols are those in which the R of the number 2 position is hydrogen or a methyl group and at least one of the other R's is hydrogen and the remaining R group is selected from alkyl, cycloalkyl, or aralkyl groups having 1 to 17 carbon atoms, more preferably 1 to 10 carbon atoms.

The upper limit on the total carbon number of the suitable 2-alcohols is basically related to their ability to be vaporized under reasonable conditions. Thus extremely high boiling alcohols would be difficult if not impossible to use. Under very high vacuum, it is conceivable that alcohols having 30, 40, and even 50 carbon atoms per molecule could be employed. However, the preferred alcohols are those having no more than 20 carbon atoms per molecule.

A list of typical 2-alcohols meeting the requirements of the preceding general formula are disclosed in columns 3 and 4 of U.S. Pat. No. 3,283,027, the disclosure of which is incorporated herein by reference.

The catalytic metal oxides can be deposited on the support in any suitable manner known in the art. The most common technique involves the deposition of a salt of the catalytic metal on the support followed by decomposition of the salt to an oxide of the catalytic metal. The currently preferred technique involves the use of a nitrate of the catalytic metal. An aqueous solution of the metal nitrate is poured over the support. After soaking for 30 minutes to an hour, the solution is concentrated by evaporation, and then the support containing the catalytic metal is dried in the presence of oxygen under such conditions that the metal salt is converted to the metal oxide. Typically, this involves heating in air at a temperature in the range of 300° C. to about 600° C.

The amount of catalytic metal oxide that can be employed in the present invention can vary over a wide range, with any catalytically effective amount being suitable. Typically, the total amount of the above defined catalytically active metal oxide is such that the total amount of the metal of catalytic metal oxide is in the range of about 0.5 to about 30 weight percent based on the weight of the support. More preferably, the total amount of the metal of the catalytic metal oxide is in the range of about 2 to about 25 weight percent based on the weight of the support.

A particularly preferred embodiment of the present invention involves the employment of a catalyst containing both cerium and thorium. In such catalysts, it is generally preferred for the weight percent of thorium to be in excess of the weight percent of the cerium. Typically for best results, the weight ratio of thorium to cerium should be in the range of ½ to 30/1, more preferably about 1/1 to 10/1. In such catalysts particularly good results have been obtained using about 5 to about 20 weight percent thorium based on the weight of the support.

As mentioned earlier, a particularly preferred embodiment of this invention involves the use of a support that has been treated with a basic compound of a metal of Groups I and II of the Periodic Table. The amount of basic compound that can be employed can vary over a wide range; however, the conversion in the dehydration reaction appears to be inversely related to the level of basic compound. Accordingly, it is generally preferred that the amount of basic compound deposited on the support be no more than about 4 weight percent based on the weight of the support prior to the base treatment. Typical examples of basic compounds of Groups I and II include potassium hydroxide, cesium carbonate, sodium hydroxide, calcium hydroxide, and magnesium carbonate. The presently preferred basic compound is potassium hydroxide.

Since many of the preferred catalysts of the present invention employ a support that has been based treated, it is here noted that in this disclosure and the foregoing claims when a reference is made to the amount of a particular metal component, such as thorium, in terms of weight percent based on the weight of the support that is intended to refer to the weight of the support prior to any base treatment.

The basic compound can also be added to the support in any suitable manner. Presently, the preferred technique involves soaking the support with an aqueous solution of the basic compound prior to the addition of the catalytic metal.

Another embodiment of the present invention is based upon the discovery that one can obtain a catalyst having high selectivity to α-olefin even with aluminum oxide-containing supports having surface areas greater than 20 m$^2$/gm by subjecting the support to base treatment and depositing thorium oxide and cerium oxide thereon. The techniques of catalyst preparation and the levels of the various catalyst components are the same as set forth previously for the catalysts prepared from the low surface area supports. Examples of such larger surface area supports are those alumina supports consisting essentially of alumina and having surface area in the range of about 100 to about 350 m$^2$/gm.

In the dehydration of 2-alcohols with the catalysts of the present invention, the alcohol in a vapor state is passed in contact with the catalyst. The temperature at which the reaction is conducted is determined by a number of variables, the most important of which are the nature of the alcohol reactant, the residence time, and the extent of conversion desired. These variables can be readily ascertained for each alcohol by those skilled in the art by routine tests.

Generally, however, reaction temperature in the range of 330° C. to 600° C. are suitable, with temperatures in the range of 350° C. to 450° C. being preferred. The present catalysts can be employed at subatmospheric pressures and superatmospheric pressures, but are most desirable since even at atmospheric pressure they allow conversions and selectivities that were not attainable with the prior art catalysts.

A further understanding of the present invention and its advantages will be provided by the following examples. In the following examples, unless stated otherwise, if the aluminum oxide support is base treated, the general technique employed involved soaking 100 gm of the support with a 50 mL aqueous solution of a basic compound such as KOH for about 30 minutes. The liquid was poured off and the support washed three times with 50 to 100 mL aliquots of water.

The catalytically active metal was added to the support, after the base treatment, if a base treated support was employed. The general technique involved soaking 100 gms of the support with 50 mL of an aqueous solution of a nitrate of the catalytically active metal. After soaking for about 30 minutes, the solution was concentrated by evaporation, and then the support was dried in air at about 350° C. for about 3 hours.

The dehydration reactions were carried out in a reactor tube ½" in diameter and 20" long that was packed with 40 gm of the catalyst. Alcohol reactant was introduced into the reactor tube at a rate of 36 mL/hr. A nitrogen sweep of 60 mL/min was employed.

Several different aluminum oxide containing supports are used in the following examples. The following table sets forth some of the characteristics of the supports:

| Support | Manufacturer | Composition, % | | | Surface Area, $m^2/gm$ |
| --- | --- | --- | --- | --- | --- |
| | | $Al_2O_3$ | $SiO_2$ | $Na_2O$ | |
| R268* | Norton | 86.0 | 12.4 | — | 0.6 |
| T1370 | Girdler | 95.0 | .1–1.0 | .3–3.0 | 188.0 |
| H151 | Alcoa | 98.0 | 1.2 | 0.7 | 324.0 |
| 60-503 | Union Carbide (Linde) | 99.85 | 0.1 | 0.003 | 215 |
| 61-501 | Union Carbide (Linde) | 99.75 | 0.15 | 0.01 | 230 |

*A Phillips' identification number for Norton's SA-5123.

EXAMPLE I

In one experiment, 0.6 weight percent Li was deposited on the Linde 60-503 support in the form of an aqueous solution of lithium hydroxide. After soaking for about 30 minutes, the solution was concentrated by evaporation and the support dried in air at 120° C. for about 8 hours. The resulting base-treated support was then evaluated as a catalyst for the dehydration of 4-methyl-2-pentanol at atmospheric pressure. At temperatures of 300° C. and 310° C., the conversion of the alcohol was 100%. About 99.5 percent of the alcohol was converted to olefins. However, the 4-methyl-1-pentene, accounted for no more than 39.2 percent of the olefins whereas the internal olefin isomer, 4-methyl-2-pentene accounted for 60 to 62 percent of the olefin product. This illustrates that the base-treated alumina oxide alone is selective for the more thermodynamically favored internal olefin.

EXAMPLE II

In another experiment, a series of catalysts were prepared by treating various aluminum oxide supports with thorium nitrate. The catalysts were then employed in the dehydration of 4-methyl-2-pentanol. The results are summarized in Table I.

TABLE I

| Support | Th, Wt. %** | Temp, °C. | Pressure | Alcohol Conversion, % | Olefin Selectivity, *% | | |
| --- | --- | --- | --- | --- | --- | --- | --- |
| | | | | | Total | 4-MP-1 | 4-MP-2 |
| R268 | 19.3 | 400 | Atm. | 89.6 | 82.4 | 95.8 | 3.9 |
| R268 | 19.3 | 410 | Atm. | 98.4 | 89.3 | 94.3 | 4.0 |
| T1370 | 9.7 | 290 | 30 psig | 15.6 | n.d. | n.d. | n.d. |
| T1370 | 9.7 | 330 | 30 psig | 57.7 | n.d. | n.d. | n.d. |
| T1370 | 9.7 | 365 | 30 psig | 92.4 | 90.2 | 59.3 | 40.0 |
| T1370 | 19.3 | 290 | 30 psig | 8 | n.d. | n.d. | n.d. |
| T1370 | 19.3 | 330 | 30 psig | 40 | n.d. | n.d. | n.d |
| T1370 | 19.3 | 350 | 30 psig | 92.1 | 82.4 | 46.2 | 53.5 |
| H151*** | 5.3 | 280 | Atm. | 100 | 99 | 31.3 | 67.2 |
| H151*** | 5.3 | 300 | Atm. | 99.5 | 98.5 | 30.5 | 67.1 |
| H151*** | 5.3 | 320 | Atm. | 98.6 | 96.6 | 27.8 | 66.9 |

*In this table and the following tables, Total is the percent of alcohol converted to olefin. The values under 4-MP-1 and 4-MP-2 refer to the percentage of the total olefin product represented by that particular olefin.
**Weight percent of Th as metal, based on the weight of the support.
***Thorium solution also contained 6 weight percent oxalic acid.

This example indicates that the effect of thorium on the dehydration reaction is much different for the low surface area support than the higher surface area supports. The ratio of the 4-methyl-1-pentene to the 4-methyl-2-pentene is surprisingly higher for the low surface area support, i.e., Norton's R268.

EXAMPLE III

Another experiment was conducted using a series of catalysts prepared by treating those supports with potassium hydroxide and then with thorium nitrate. The effects of those catalysts on the dehydration of 4-methyl-2-pentanol are set forth in Table II.

TABLE II

| Support | Th, Wt. % | K, Wt. % | Temp, °C. | Pressure | Alcohol Conversion, % | Olefin Selectivity, % | | |
| --- | --- | --- | --- | --- | --- | --- | --- | --- |
| | | | | | | Total | 4-MP-1 | 4-MP-2 |
| R268 | 19.3 | 2.8 | 370 | Atm. | 37.0 | 36.1 | 99.3 | 0.4 |
| R268 | 19.3 | 2.8 | 402 | Atm. | 69.7 | 67.1 | 99.2 | 0.4 |
| R268 | 19.3 | 2.8 | 412 | Atm. | 75.2 | 71.6 | 99.5 | 0.3 |
| R268 | 19.3 | 2.8 | 422 | Atm. | 85.5 | 81.3 | 99.6 | 0.3 |
| R268 | 19.3 | 2.8 | 434 | Atm. | 93.0 | 87.9 | 99.6 | 0.3 |
| R268 | 19.3 | 2.8 | 444 | Atm. | 95.6 | 90.2 | 99.4 | 0.3 |
| R268 | 19.3 | 2.8 | 446 | Atm. | 90.9 | 85.8 | 99.4 | 0.4 |
| R268 | 19.3 | 1.4 | 340 | 30 psig | 13.0 | n.d. | n.d. | n.d. |
| R268 | 19.3 | 1.4 | 370 | 30 psig | 29.8 | 28.8 | 99.0 | 0.5 |
| R268 | 19.3 | 1.4 | 397 | 30 psig | 51.5 | 48.8 | 99.2 | 0.4 |

A comparison of the results in Table II with those in Table I reveals that the base treatment of the supports results in a slight decrease in the overall conversion of the alcohol but an increase in the selectivity to the alpha olefin. Accordingly, by using the base treatment and slightly higher reaction temperatures, one can obtain higher yields of the alpha olefin than can be obtained at similar levels of alcohol conversion with a catalyst of thorium on a support which had not been base treated.

EXAMPLE IV

Another catalyst was prepared by depositing thorium and cerium on the Norton R268 support. The thorium was deposited in an amount equal to 19.3 weight percent of the support. The cerium was deposited in an amount equal to 3.2 weight percent of the support. The effectiveness of this catalyst in the dehydration of 4-methyl-2-pentanol at atmospheric pressure is shown in Table III.

TABLE III

| Temp, °C. | Alcohol Conversion, % | Olefin Selectivity, % | | |
|---|---|---|---|---|
| | | Total | 4-MP-1 | 4-MP-2 |
| 370 | 65.1 | 61.8 | 98.8 | neg. |
| 400 | 92.1 | 86 | 98.7 | neg. |
| 410 | 96.7 | 91 | 98.9 | neg. |

A comparison of the results of Table III with those in Tables I and II reveals that the alcohol conversion is slightly better for the Th-Ce catalyst than for the corresponding Th-base treated catalyst of Table II and the selectivity to 4-methyl-1-pentene is slightly better for the Th-Ce catalyst than for the corresponding non-base treated Th catalyst of Table I.

EXAMPLE V

In yet another series of runs, 19.3 weight percent thorium and 3.2 weight percent cerium were deposited on aluminum oxide supports that were pretreated with KOH. The results obtained when the catalysts were used to dehydrate 4-methyl-2-pentanol at atmospheric pressure are shown in Table IV.

TABLE IV

| Support | K, Wt. % | Temp, °C. | Alcohol Conversion, % | Olefin Selectivity, % | | |
|---|---|---|---|---|---|---|
| | | | | Total | 4-MP-1 | 4-MP-2 |
| R268 | 2.8 | 370 | 63.6 | 61.8 | 99.3 | neg. |
| R268 | 2.8 | 400 | 89.2 | 86.2 | 99.6 | neg. |
| R268 | 2.8 | 410 | 95.4 | 91.6 | 99.6 | neg. |
| R268 | 1.4 | 370 | 64.9 | 62.6 | 99.6 | neg. |
| R268 | 1.4 | 390 | 84.9 | 80.8 | 99.6 | neg. |
| R268 | 1.4 | 410 | 96.7 | 91.1 | 99.6 | neg. |
| 60-501 | 1.4 | 400 | 73.7 | 69.4 | 99.6 | 0.4 |
| 60-501 | 1.4 | 420 | 90.2 | 84 | 84.6 | 14.7 |

A comparison of the results obtained with the low surface area Norton R268 support in this example with the results of Example IV, reveals that while the alcohol conversion is slightly lower for the base treated Th-Ce catalyst of this Example than for the Th-Ce catalyst of Example IV, the selectivity to the alpha olefin is slightly better. Accordingly, where high yields of the α-olefin are desired, the preferred catalyst would be one having been treated with Th, Ce, and base.

The above results also show that the combination of Th, Ce, and base can even improve the 4-MP-1 selectivity of a catalyst prepared from the higher surface area Linde 61-501 support. In Example II, it will be recalled, the high surface area Th-containing supports gave olefin products in which the α-olefin was either less than half of the olefin product or only slightly more than half.

EXAMPLE VI

Another series of catalysts were employed in the dehydration of 2-methyl-2-butanol. All the reactions were carried out at atmospheric pressure, employing a 36 mL/hr feed rate of 2-methyl-2-butanol, and 60 ml/min nitrogen flow rate. Reaction temperature, feed alcohol conversions and selectivities to 2-methyl-1-butene are set forth in Table V. The major reaction by-product is 2-methyl-2-butene.

TABLE V

| Support | Th, Wt. % | Ce, Wt. % | K, Wt. % | Temp, °C. | Alcohol Conversion, % | α-Olefin, %* |
|---|---|---|---|---|---|---|
| R268 | 19.3 | — | 0.7 | 350 | 99 | 64.3 |
| R268 | 19.3 | — | 0.3 | 350 | 99.1 | 57.9 |
| R268 | 10.0 | — | 7.0 | 350 | 6.8 | n.d. |
| R268 | 10.0 | — | — | 450 | 81.6 | 85.4 |
| R268 | 19.3 | 3.2 | 2.8 | 360 | 85.8 | 95.4 |
| R268 | 19.3 | 3.2 | 2.8 | 380 | 99.5 | 97.5 |
| 60-503 | — | — | 0.7 | 310 | 98.0 | 47.5 |
| 60-503 | — | — | 7.0 | 310 | 82.1 | 56.5 |

*Percentage of olefin product.

The above data reveals that the selectivity to α-olefin of the base treated low surface area Th-containing catalyst was better than that of the base treated high surface area catalyst. The data further illustrates that the selectivity to the α-olefin is even better if Ce is employed in conjunction with the Th and base treatment.

EXAMPLE VII

The data presented in the foregoing examples and the prior art make it quite clear that in the dehydration of 4-methyl-2-pentanol, it is possible to obtain wide variations in the ratio of alpha olefin to internal olefin by the use of various types of catalysts. This fact can be applied to provide a process for the coproduction of selected ratios of 4-methyl-1-pentene and 3-methyl-1-butene, two specialty chemicals for which there is considerable demand. The process involves the dehydration of the 4-methyl-2-pentanol to obtain a mixture of 4-methyl-1-pentene and 4-methyl-2-pentene followed by the disproportionation of that olefin mixture with ethylene. Typically, it is desirable to remove substantially all the other dehydration reaction products and unreacted alcohol from the mixture of 4-methyl-1-pentene and 4-methyl-2-pentene prior to subjecting that mixture to the disproportionation reaction. Any suitable conditions can be employed in the disproportionation reaction. Typical conditions are disclosed in U.S. Pat. Nos. 3,457,320 and 3,658,932, the disclosures of which are incorporated herein by reference.

Thus, if one employs a dehydration catalyst of the type disclosed herein which gives an olefin product in which substantially all the olefin is 4-methyl-1-pentene, the coproduction process results mainly in 4-methyl-1-pentene. The coproduction process does however allow for the recovery of a more pure 4-methyl-1-pentene since it is much easier to separate 3-methyl-1-butene from 4-methyl-1-pentene by distillation than it is to separate 4-methyl-2-pentene from 4-methyl-1-pentene.

By employing a dehydration catalyst that gives an approximately 1:1 ratio of 4-MP-1 to 4-MP-2, one can obtain a product from the metathesis reaction, a product having 4-MP-1, 3-MB-1, and propylene in about a 1:1:1 ratio.

By employing a dehydration catalyst that gives about a 2:1 ratio of 4MP-2 to 4-MP-1, one can obtain a product from the metathesis reaction having a 3-MB-1 to 4-MP-1 ratio of around 2/1.

Accordingly by simply varying the dehydration catalyst, it is possible to vary the relative yields of 3-MB-1 and 4-MP-1 over a wide range. A corresponding benefit is that the 4-MP-1 can be more readily recovered as a substantially pure product than it can from the reaction product of the dehydration reaction.

EXAMPLE VIII

Another series of catalysts were prepared using Th and Ce and other base treated low surface area aluminum oxide containing supports obtained from Norton. The supports and their relevant properties are summarized in Table VI.

TABLE VI

| Support | Composition, Wt. % | | Surface Area, |
| --- | --- | --- | --- |
| | Al$_2$O$_3$ | SiO$_2$ | m$_2$/gm |
| SA-5102 | 87 | 11 | 0.3 |
| SA-5158 | 99 | — | 0.7 |
| SA-3235 | 80 | 18 | 14 |

These catalysts, like the other previously discussed inventive catalysts, gave conversions of more than 90% with the 4-MP-1 product being the predominant olefin formed. The selectivity to 4-MP-1 was lower for the higher surface area support SA-3235.

What is claimed is:

1. A process for preparing an α-olefin comprising contacting a dehydratable 2-alcohol under suitable reaction conditions with a catalyst selected from the group consisting of catalysts comprising a catalytically effective amount of at least one catalytic metal selected from the group consisting of metals having atomic numbers of 21, 39, 58–71, or 90 supported on a support consisting essentially of an oxide of aluminum having a surface area no greater than 20 m$^2$/g.

2. A process according to claim 1 wherein the total amount of said catalytic metal oxide is in the range of 0.5 to about 30 weight percent based on the weight of the support.

3. A process according to claim 2 wherein thorium oxide is employed.

4. A process according to claim 3 wherein the catalytic metal oxide consists essentially of thorium oxide.

5. A process according to claim 3 wherein said catalyst contains thorium oxide and cerium oxide.

6. A process according to claim 5 wherein the catalytic metal oxide consists essentially of thorium oxide and cerium oxide, the level of thorium is in the range of about 5 to about 20 weight percent based on the weight of the support, and the weight ratio of thorium to cerium is in the range of about ½ to about 30/1.

7. A process according to claim 6 wherein the support has been base treated.

8. A process according to claim 7 wherein potassium hydroxide is used in the base treatment.

9. A process according to claim 8 wherein said catalyst is prepared by soaking a support comprising alumina having a surface area no greater than 20 m$^2$/g with an aqueous solution of potassium hydroxide, then washing the support with water, then washing the support with an aqueous solution of cerium nitrate and thorium nitrate, then evaporating the water, and then calcining at a temperature in the range of 300° C. to about 600° C.

10. A process according to claim 9 wherein said 2-alcohol consists essentially of 4-methyl-2-pentanol or 2-methyl-2-butenol.

11. A process according to claim 10 wherein said catalyst contains about 19 weight percent thorium based upon the weight of said support and about 3 weight percent cerium metal based on the weight of said support.

12. A process according to claim 3 wherein said alcohol consists essentially of 4-methyl-2-pentanol.

13. A process according to claim 4 wherein said support has been base treated.

14. A process according to claim 4 wherein said 2-alcohol consists essentially of 4-methyl-2-pentanol.

15. A process according to claim 13 wherein said 2-alcohol consists essentially of 4-methyl-2-pentanol.

16. A process according to claim 6 wherein said 2-alcohol consists essentially of 4-methyl-2-pentanol.

17. A process according to claim 7 wherein said 2-alcohol consists essentially of 4-methyl-2-pentanol.

18. A process according to claim 1 wherein said 2-alcohol has less than 30 carbon atoms per molecule.

19. A process according to claim 18 wherein said 2-alcohol is of the formula

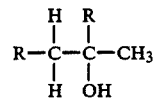

wherein the R in the 2 position is hydrogen or a methyl radical and the other R is an alkyl, cycloalkyl, or aralkyl group having 1 to 17 carbon atoms.

20. A process according to claim 19 wherein said 2-alcohol consists essentially of 4-methyl-2-pentanol.

21. A process according to claim 19 wherein said 2-alcohol consists essentially of 2-methyl-2-butanol.

22. A process according to claim 20 wherein the mixture of 4-methyl-1-pentene and 4-methyl-2-pentene resulting from the dehydration is contacted with ethylene in the presence of a disproportionation catalyst under conditions sufficient to convert said 4-methyl-2-pentene to a mixture of 3-methyl-1-butene and propylene.

23. A process according to claim 22 wherein the 4-methyl-1-pentene in the reaction product of the disproportionation reaction is separated from the remainder of the reaction product.

24. A process for preparing an α-olefin comprising contacting a dehydratable 2-alcohol under suitable reaction conditions with a catalyst comprising base treated aluminum oxide having deposited thereon a catalytically effective amount of a mixture of thorium oxide and cerium oxide.

25. A process according to claim 24 wherein said 2-alcohol has less than 30 carbon atoms per molecule.

26. A process according to claim 25 wherein said 2-alcohol is of the formula

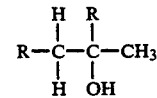

wherein the R in the 2 position is hydrogen or a methyl radical and the other R is an alkyl, cycloalkyl, or aralkyl group having 1 to 17 carbon atoms.

27. A process according to claim 26 wherein said 2-alcohol consists essentially of 4-methyl-2-pentanol.

28. A process according to claim 26 wherein said 2-alcohol consists essentially of 2-methyl-2-butanol.

29. A process according to claim 27 wherein said 2-alcohol consists essentially of 4-methyl-2-pentanol.

30. A process according to claim 27 wherein the mixture of 4-methyl-1-pentene and 4-methyl-2-pentene resulting from the dehydration is contacted with ethylene in the presence of a disproportionation catalyst under conditions sufficient to convert said 4-methyl-2-pentene to a mixture of 3-methyl-1-butene and propylene.

31. A process according to claim 30 wherein the 4-methyl-1-pentene in the reaction product of the disproportionation reaction is separated from the remainder of the reaction product.

32. A process according to claim 24 wherein said support has a surface area in the range of 100 to 350 $m^2/g$ and said catalyst contains about 5 to 20 weight percent of thorium metal based on the weight of the support and further being characterized by containing cerium in such an amount that the weight ratio of thorium to cerium is in the range of ½ to 30/1.

33. A process according to claim 32 wherein the base treatment is provided by potassium hydroxide.

34. A process according to claim 33 wherein said catalyst contains about 19 weight percent thorium metal based on the weight of said support and about 3 weight percent cerium metal based on the weight of said support, and wherein the support has a surface are of about 230 $m^2/g$ and comprises about 99.75 weight percent aluminum.

35. A process according to claim 34 where in said 2-alcohol consists essentially of 4-methyl-2-pentanol.

* * * * *

UNITED STATES PATENT AND TRADEMARK OFFICE
CERTIFICATE OF CORRECTION

PATENT NO. : 4,490,567

DATED : Dec. 25, 1984

INVENTOR(S) : Charles A. Drake

It is certified that error appears in the above-identified patent and that said Letters Patent is hereby corrected as shown below:

Column 9, line 65 (claim 10), "2-methyl-2-butenol" should read --- 2-methyl-2-butanol ---.
Column 10, line 67 (claim 29), "27" should read --- 32 ---.

Signed and Sealed this

Twenty-first Day of May 1985

[SEAL]

Attest:

DONALD J. QUIGG

Attesting Officer          Acting Commissioner of Patents and Trademarks